United States Patent [19]

Hartdegen et al.

[11] 4,094,744

[45] June 13, 1978

[54] WATER-DISPERSIBLE PROTEIN/POLYURETHANE REACTION PRODUCT

[75] Inventors: Frank Joseph Hartdegen, Columbia; Wayne Elliott Swann, Pasadena, both of Md.

[73] Assignee: W. R. Grace & Co., New York, N.Y.

[21] Appl. No.: 749,430

[22] Filed: Dec. 10, 1976

Related U.S. Application Data

[63] Continuation-in-part of Ser. No. 743,035, Nov. 18, 1976, which is a continuation-in-part of Ser. No. 660,982, Feb. 24, 1976, abandoned, which is a continuation-in-part of Ser. No. 585,674, Jun. 10, 1975, abandoned.

[51] Int. Cl.² .............................................. C07G 7/02
[52] U.S. Cl. ..................................... 195/63; 195/68; 195/DIG. 11; 260/112 R
[58] Field of Search ...................... 195/63, 68, DIG. 4; 260/112 R

[56] References Cited

U.S. PATENT DOCUMENTS

| 3,672,955 | 6/1972 | Stanley | 195/68 |
| 3,928,138 | 12/1975 | Wood et al. | 195/68 |

*Primary Examiner*—David M. Naff
*Attorney, Agent, or Firm*—Philip M. Pippenger; William W. McDowell, Jr.

[57] ABSTRACT

An aqueous dispersion of a biologically-active protein bound to polyurethane is formed by (a) admixing the protein and an isocyanate-capped liquid polyurethane prepolymer to form a solution; and (b) dispersing the solution in water.

19 Claims, No Drawings

WATER-DISPERSIBLE PROTEIN/POLYURETHANE REACTION PRODUCT

The present application is a continuation-in-part of pending U.S. Patent Application Ser. No. 743,035 filed Nov. 18, 1976 by Frank J. Hartdegen and Wayne E. Swann — "PROCESS FOR IMMOBILIZING PROTEINS", which is a continuation-in-part of Ser. No. 660,982, now abandoned filed Feb. 24, 1976, which is in turn a continuation-in-part of Ser. No. 585,674, filed June 10, 1975 (now abandoned).

Also related to the above series of applications is pending application Ser. No. 644,025 by Frank J. Hartdegen and W. E. Swann, filed Dec. 24, 1975 for an invention entitled, "IMMOBILIZED BIOLOGICAL MATERIAL".

BACKGROUND OF THE INVENTION

1. Field of the Invention

This invention relates to proteins. More particularly, it relates to proteins modified by attachment to organic polymers. Even more particularly, this invention relates to: (a) such a protein which has been modified by contacting it with an isocyanate-capped liquid polyurethane prepolymer to form a reaction product which is soluble or dispersible in water. Still more particularly, this invention relates to such protein and such process where said protein is an enzyme, an antibody, or an antigen and the polymer is a poly(urea-urethane).

The aqueous dispersions of protein/polymer reaction product are formed by dissolving the protein in an isocyanate-capped liquid polyurethane prepolymer and dispersing the resulting solution in water.

2. Description of the Prior Art

A review of enzyme technology was published in the Aug. 18, 1975 issue of Chemical & Engineering News (pp. 22–41).

The term "soluble bound enzymes" is employed in the prior art to designate the reaction product of a protein with a polymeric material (natural or synthetic). The reaction product is soluble or dispersible in liquid media, usually water. The protein/polymer bond is generally covalent although adsorption techniques have also been employed. The soluble bound proteins frequently exhibit biological reactivity similar in nature to that of the free protein. Some of the soluble bound proteins have exhibited increased solubility, and/or decreased antigenicity and other improvements in comparison with the free unmodified proteins.

In a published thesis (M. G. Brattain, Rutgers University, 1974 — Modification of L-Asparaginase by Water Soluble Polymers) bonding via cyanuric chloride of asparaginase to polyethylene glycols and other polymers is described. The bound products are water-dispersibleand exhibit some improvement in stability as well as decreased antigenicity. The present invention is similarly concerned with binding enzymes to polyethylene glycols although the method of bonding and method of production differs greatly from the teachings of the Brattain thesis.

Additionally U.S. Pat. No. 3,574,062 (195/63, Sato) teaches a method for preparing a bound protein (an enzyme) wherein a polyester polyurethane is diazotized with a diazonium salt of an amino acid and then coupled with a nonenzymatic animal protein to form a diazotized polyurethane which is reacted with an enzyme to form the immobilized enzyme.

U.S. Pat. No. 3,705,084 (195/63, Reynolds) teaches a flow-through enzyme reactor comprising: (a) a macroporous reactor core; (b) a polymeric surface (which can be a polyurethane resin) on the reactor core; (c) an enzyme adsorbed on the polymeric surface and cross-linked in place thereon by a difunctional agent (e.g. a polyisocyanate).

Reynolds prepares the immobilized enzyme for his reactor by adsorbing an active enzyme on a polymeric surface and further immobilizing the enzyme by cross-linking it is place with a crosslinking agent such as a monomeric polyisocyanate.

German Offenlegungsschrift No. 2,319,706 published Nov. 15, 1973 teaches an enzyme bound to a polyurethane foam and a method for preparing such bound enzyme.

U.S. Pat. No. 3,791,927 (195/68, forgione et al) teaches a water-insoluble bound protein (enzyme) entrapped within the cells of a self-supporting reticulated cellular material (which can be a polyurethane foam), the protein (enzyme) being bound to the cellular material.

U.S. Pat. No. 3,672,955 (195/68, Stanley) teaches a process for preparing a bound protein (enzyme) comprising: (a) emulsifying an aqueous dispersion of the enzyme with a solution of a polyisocyanate in a volatile water-immiscible solvent (e.g., methylchloroform); (b) admixing the resulting emulsion with a solid particulate carrier; and (c) evaporating the solvent therefrom. Stanley's polyisocyanate can be an isocyanate-capped liquid polyurethane prepolymer. Said U.S. Pat. No. 3,672,955, in its entirety, is incorporated herein by reference.

It is noted that, in his Example 3, Stanley reports the binding of an enzyme component (a peroxidase) of a fermentation broth by admixing a portion of the broth with a polyisocyanate dissolved in methylchloroform. It seems probable that, under Stanley's reaction conditions, any other enzymes which were present in the broth would have been immobilized (rendered insoluble in water, i.e., bound).

Silman et al, Annual Review of Biochemistry, 1966, 35 (Part 2), pages 873–908 presents a review of methods for preparing water-insoluble derivatives of enzymes, antigens, and antibodies.

Singer, Nature, 1959, 183, 1523–1524 teaches a method for reacting a protein with a diisocyanate (m-xylene diisocyanate).

U.S. Patent Application Ser. No. 250,012, filed May 3, 1972, and now abandoned (Wood et al, inventors) which is assigned to W. R. Grace & Co. teaches, in Example 21, a foamed polyurethane comprising an immobilized enzyme (urease), a method for preparing such immobilized enzyme, and a method for using it.

Said Application Ser. No. 250,012 also teaches, e.g. in Claim 8, a foamable composition comprising: (a) an isocyanate-capped polyurethane prepolymer; (b) water; and (c) biostats, fungicides, or enzymes. A similar teaching occurs in claim 7 of the above-mentioned German Offenlegungsschrift No. 2,319,706.

U.S. Pat. No. 3,929,574, Wood et al, teaches the preparation of a bound (immobilized) protein, an enzyme, by a process comprising contacting an isocyanate-capped liquid polyurethane prepolymer with an aqueous dispersion of the enzyme under foam-forming conditions, whereby the polyurethane foams and the enzyme become integrally bound to the resulting polyurethane foam.

It is noted that, in said U.S. Pat. No. 3,929,574, Wood et al reports, in Example 1, that an enzyme (cellulase) present in a fermentation broth was immobilized (bound or rendered insoluble) by admixing the broth with an isocyanate-capped liquid polyurethane prepolymer under conditions which produced a foam. It seems probable that, under the conditions of said Example 1, any other enzymes present in the broth would have been immobilized.

U.S. Pat. No. 3,905,923 (260/2.5 AD, Klug) teaches an immobilized enzyme system formed from an enzyme and a hydrophilic poly(urea-urethane) foam, the foam surrounding, entrapping, and supporting the enzyme in an active configuration. The hydrophilic foam is formed by the reaction of water with a hydrophilic isocyanate-capped polyoxyalkylene prepolymer.

Isocyanate-capped polyurethane prepolymers are well known to those skilled in the art. See for example: (a) the penultimate paragraph on page 854 of Volume 9 of the Second Edition of the Kirk-Othmer "Encyclopedia of Chemical Technology", John Wiley and Sons, Inc., New York, N. Y., or (b) the third full paragraph in the left-hand (first) column of page 872 of the Second Edition of "The Encyclopedia of Chemistry", George L. Clark, Editor, Reinhold Publishing Corporation, New York, N. Y.

T. Richard and N. F. Olson, "Immobilized Enzymes in Food and Microbial Processes", Plenum Press, New York, N. Y., 1974, pages 35–36 teach the formation of a bound (immobilized) enzyme by reacting the enzyme, water, and a polyisocyanate polymer.

Weetall, Journal of Bacteriology, volume 93, pages 1876–1880 (1967) teaches the isolation and purification of large quantities of bacterial specific antibodies by using polymerized microorganisms as a specific immunoadsorbent. The microorganisms were polymerized by reaction with tetrazotized benzidine.

SUMMARY OF THE INVENTION

This invention is directed to aqueous dispersions of water-dispersible, biologically-active proteins bound to a polyurethane having an essentially linear polyoxyalkylene or polyester backbone. The dispersions are prepared by admixing a water-dispersible, biologically-active protein and an isocyanate-capped liquid polyurethane prepolymer under essentially anhydrous conditions to form a solution. The solution is dispersed into water and any insoluble material can be separated (e.g. by filtration). The invention is directed to achieving water-dispersible protein/polymer compounds by means of preliminary formation of a protein/prepolymer solution. Formation of the solution is an essential part of the present invention. Solution formation is also disclosed in copending Application Ser. No. 743,035 filed Nov. 18, 1976 (PROCESS FOR IMMOBILIZING PROTEINS by F. Hartdegen and W. Swann) and solution formation is also an essential portion of that invention. The invention of the copending application involves formation of foams wherein proteins are bound. The present invention is an improvement over the invention of said copending application in the sense that water-dispersible or water-soluble compositions are disclosed.

The process for producing the water-dispersible compounds is conducted at a temperature at which the isocyanate-capped liquid polyurethane prepolymer exists in the liquid state and at a temperature below the denaturation temperature of the protein which is being bound.

In the dispersible compounds it is believed that the protein is bound to the polyurethane polymer through at least one ureido linkage. As set forth in the examples it is apparent that a protein/polyurethane product has been formed which has different characteristics, e.g. migration through a chromatographic column, migration in an electric field, and solubility properties, than are possessed by either the free protein or the free polymer. It is known that the reaction rates of amines with isocyanate groups are much faster than reaction rates between amines and water or hydroxyl groups (compare pages 140, 177 and 184 of Saunders and Frisch, vol. 1, "Polyurethanes: Chemistry and Technology", published 1962 by Interscience Publishers).

It is also known that proteins e.g. enzymes, antigens, antibodies and simple proteins (e.g. serum albumins) are essentially polymers of amino acids having available $-NH_2$ groups. Therefore, it is likely that in the protein/prepolymer solution ureido linkages form between the protein and the prepolymer.

Upon being dispersed in water unreacted —NCO groups are converted to $-NH_2$ by reaction with water. Therefore, the protein/prepolymer solution is dispersed into enough water at a rate sufficiently slow so that chain extension is minimized. The method of dispersion is not critical except that to minimize chain extension dispersion should be accompanied by agitation, and addition of the prepolymer solution to the water should be conducted at a practical rate which is sufficiently slow to allow dispersion and minimize chain extension. It has been found that chain extension does occur to give insoluble material which is separated by filtration. To increase yields of soluble compounds, adequate dispersion conditions should be maintained.

Additionally to promote dispersion a surfactant may be employed. The use of surfactants as employed in the present invention represents conventional technology with the only caveat being that the surfactant should not interact with the protein to decrease biological activity. Suitable surfactant include nonionic materials such as those represented by the complex mixture of polyoxyethylene derivatives sold under the trade name "Tween". Also useful are the block copolymers of oxyethylene/oxypropylene sold under the trade name "Pluronic". The surfactant can be added either to the water, or the protein/prepolymer solution.

In dispersing the protein/prepolymer solution in water, it frequently happens that the protein/polymer reaction product is water soluble. This is especially the case where the backbone of the polyurethane contains any appreciable number of oxyethylene units, e.g., 50% or more on a weight basis. The term "dispersions" as used herein includes aqueous "solutions" of the protein/polymer reaction product. On the other end of the spectrum for reaction products which are at least partially insoluble and are difficult to disperse, a surfactant can be employed as described above.

In admixing the protein and prepolymer the relative amount of NCO groups in relation to $NH_2$ groups of the protein is not critical. An excess of NCO groups can be employed. By excess it is meant that sufficient isocyanate is employed so that after dissolving the protein in the prepolymer, there is unreacted free —NCO more than one hour after the solution has been formed assuming the components were admixed and allowed to dissolve at ambient temperature, e.g. 70° F. If the excess of NCO groups is too large, the likelihood of chain extension on dispersing in water is increased. The possibility of forming insoluble reaction products is also increased. Preferably the amount of protein amine groups will be in excess. This reduces the number of polymer chains attached to each protein molecule. It is believed that the advantages (e.g. stabilization, reduced antigenicity) of polymer-modified proteins can be accomplished equally well whether one or a large number of polymer chains are bound to the protein. Also the likelihood of forming difficulty-dispersible species on addition to water is reduced.

It is believed that protein/polymer reaction products likely to be present in the protein/prepolymer solution include the following idealized species (where P = protein and Pol = polymer):

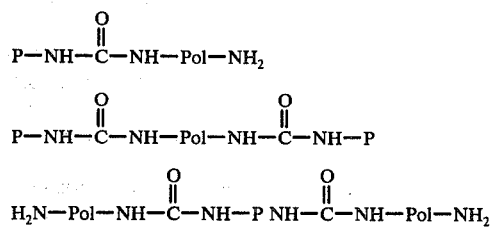

It is not unlikely, especially where excess polymer is present, that the protein may serve as a center for branching resulting in the following type of idealized structure:

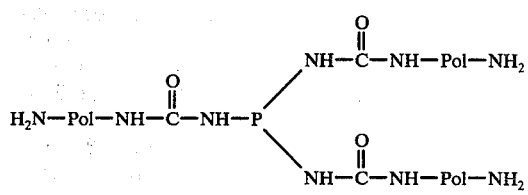

The above structures ca be extended to form an extensive network which is difficult to disperse in water. Further the presence of large numbers of polymer chains may create stearic interference, as where the protein is an enzyme and the polymer chains interfere with the approach of the substrate and the enzyme. The problem would be reduced where the substrate is small as in the case of peroxidase enzymes — such enzymes are also known to be relatively unstable. It is believed that modification of peroxidase enzymes with polyurethane according to the present invention would be beneficial.

DESCRIPTION OF PREFERRED EMBODIMENTS

In preferred embodiments of the invention recited in the above Summary:

1. The aqueous dispersion is filtered following dispersion of the protein/prepolymer solution to remove undispersed material. It is believed that the undispersed matter is primarily protein bound to polyurethane which has become difficult to disperse because of chain extension. Use of a different surfactant may be sufficient to correct this situation or preferably the dispersion is filtered. Also it is preferred to use water-soluble hydrophilic polyurethanes having at least 50 mole percent of ethylene oxide units in the backbone.

2. The isocyanate-capped liquid polyurethane prepolymer is prepared by reacting toluene diisocyanate and a polyethylene glycol.

3. The isocyanate-capped liquid polyurethane prepolymer is prepared by reacting toluene diisocyanate and a polyethylene glycol having a molecular weight (average molecular weight) of about 800–1,200 (preferably about 1,000).

4. The isocyanate-capped liquid polyurethane prepolymer is prepared by reacting toluene diisocyanate and a member selected from the group consisting of ethylene glycol, diethylene glycol, a polyoxyethylene polyol polymer, pentaerythritol, glycerol, trimethylol propane, and a polyoxypropylene polyol polymer — provided at least 50 mole percent of the backbone in polyoxyethylene.

5. The protein is an enzyme, an antibody, or an antigen.

6. The isocyanate-capped liquid polyurethane prepolymer is prepared by reacting toluene diisocyanate with an admixture of a polyethylene glycol having an average molecular weight of about 800–1,200 (preferably about 1,000) and trimethylol propane, the trimethylol propane and the polyethylene glycol being provided in a mole ratio of about 1:1–4 and the toluene diisocyanate being provided at a rate of about 0.85–1.25 (preferably 0.95–1.1) mole of toluene diisocyanate per equivalent (17 g.) of —OH provided by the polyethylene glycol plus the trimethylol propane.

7. The isocyanate-capped liquid polyurethane prepolymer can be prepared from toluene diisocyanate and ethylene glycol according to the method recited in Example 1 of above-mentioned U.S. Pat. No. 3,929,574 (Wood et al). Said patent in its entirety is incorporated herein by reference.

In another preferred embodiment ("Embodiment A") this invention is directed to a process for preparing aqueous protein/polyurethane dispersions of a protein which can be an enzyme, an antibody, or an antigen, said process comprising:

(a) forming a first product by admixing, in the absence of water (i.e., under essentially anhydrous conditions), the protein and a liquid polyisocyanate (e.g. at least one of the liquid polyisocyanates listed in Table 1, infra, or the like);

(b) forming a second product comprising an isocyanate-capped liquid polyurethane prepolymer with the protein dissolved therein by admixing and reacting, in the absence of water, the first product and an amount of a polyol effective for forming the second product (the polyol can be at least one of those listed in Table 2, infra, or the like and can include at least one of those recited in the paragraph immediately preceding said Table 2); and (c) dispersing the second product in water.

In another preferred embodiment ("Embodiment B") this invention is directed to a process for preparing an aqueous dispersion of an enzyme, an antibody, or an antigen, said process comprising:

(a) forming a first product by admixing, in the absence of water, the protein and a liquid polyol (the polyol can be at least one of those listed in Table 2, infra, or the like and can include at least one of those recited in the paragraph immediately preceding said Table 2);

(b) forming a second product comprising an isocyanate-capped liquid polyurethane prepolymer with the protein dissolved therein by reacting, in the absence of water, the first product and an amount of a polyisocyanate effective for forming the second product (the polyisocyanate can be at least one of those listed in Table 1, infra, or the like); and (c) dispersing the second product in water.

In the methods of Embodiments A and B it is generally preferred to use about 2–500 or 50–100 mg. of protein per gram of polyol. The amount of protein employed in relation to the isocyanate is not critical.

In another preferred embodiment ("Embodiment C") this invention is directed to a process for preparing aqueous dispersions of an enzyme bound to a polyurethane, said process comprising:

(a) admixing, in the absence of water, the liquid polyurethane prepolymer and a substrate reactable with the enzyme to form a first composition;

(b) admixing, in the absence of water, the first composition and the enzyme to form a second composition; and (c) dispersing the second composition in water.

In the process of Embodiment C it is generally preferred to use about 5–100 moles or 8–12 moles of substrate per mole of enzyme.

In another preferred embodiment ("Embodiment D") this invention is directed to a protein-containing aqueous dispersion comprising about 0.1 to 50% by weight of an active protein preparation on an anhydrous basis covalently bound by ureido linkages to a water-dispersible hydrophilic poly(urea-urethane) polymer having an oxyalkylene backbone containing at least 50 mole percent oxyethylene; said aqueous dispersion being formed by dispersing a solution consisting essentially of said protein dissolved in an isocyanate-terminated prepolymer (an isocyanate-capped liquid polyurethane prepolymer) in water, said protein can be selected from the group consisting of an enzyme, an antibody, and an antigen.

DETAILED DESCRIPTION OF THE INVENTION

In the process of our invention the isocyanate-capped liquid polyurethane prepolymer acts as: (a) a solvent to dissolve the protein which is to be bound; and (b) a reactant to react with the protein to bind it (the protein) to itself.

The solidification temperature of the isocyanate-capped liquid polyurethane prepolymer used in our process will vary depending on the molecular weight of the prepolymer and on the structure of the backbone of the prepolymer.

The thermal denaturation temperature of proteins is generally above about 35° C. However, some proteins are stable for relatively short periods (e.g., 5–30 minutes or longer) at higher temperatures (e.g. at temperatures up to about 70° C. or somewhat higher).

The formation of the protein/prepolymer solution is conducted in the absence of water. The solution can be formed in the presence or absence of a diluent or in the presence of a mixture of diluents. Because of our disclosure, it will be readily apparent to those skilled in the art that a diluent which would denature the protein or prevent or substantially reduce dispersibility cannot be employed. Diluents which are operable include but are not limited to those taught by Stanley (U.S. Pat. No. 3,672,955). The diluents can be very soluble in water, e.g. acetone and the like; moderately soluble in water, e.g., methyl acetate, methyl ethyl ketone, and the like; or insoluble in water, e.g. benzene and the other diluents listed in the paragraph starting on line 45 of column 1 of Stanley's above-mentioned U.S. Pat. No. 3,672,955. Said U.S. Pat. No. 3,672,955, in its entirety, is incorporated herein by reference.

Diluents serve to reduce the viscosity of: (a) the isocyanate-capped liquid polyurethane prepolymer; and (b) the resulting solution.

Where the diluent is insoluble or substantially insoluble in water, an emulsifying agent can be used during the foaming step. Stanley (U.S. Pat. No. 3,672,955) teaches the use of such emulsifying agent.

Binding of the protein by reaction with the prepolymer is believed to be a general reaction applicable to all proteins including, but not limited to, enzymes, antibodies, and antigens. For example, it is believed that the following can be bound: urease, cellulase, pectinase, papain, bromelain, chymotrypsin, trypsin, ficin, lysozyme, glycose isomerase, lactase, human immunoglobulin G, invertase, asparginase, and the like. While our work in forming aqueous dispersions has not been extensive to date, we have found no enzyme, antibody or antigen, or other protein which cannot be bound. The purity of the protein is not believed to be critical, i.e., whether pure or not it would be expected to have the requisite amine groups. Binding can be accomplished using: (a) pure crystalline protein; (b) partially purified non-crystalline protein; (c) impure dried extracts containing enzyme, antibody, or antigen activity; or (d) unpurified dried extract from a fermentation broth (e.g. an acetone precipitation product obtained from the broth). It is believed that our process can be used to bind proteins (including enzymes, antibodies, and antigens) of substantially any purity.

Following formation of the protein/prepolymer solution certain proteins will cause the prepolymer to solidify if the protein is present in sufficiently large amounts. An example of this phenomena is penicillin amidase. Where the amidase level exceeds about 10 weight percent based on the weight of the prepolymer, the prepolymer solution exhibits increased viscosity and cannot be stirred after about 60 minutes. At concentrations below about 5 weight percent, the solution can still be stirred and dispersed into water.

It has been discovered that the solidified penicillin amidase polyurethanes are biologically active, i.e., the enzyme is bound in active form. For example, 100 mg. of prepolymer 3 (see Example 2, infra), 100 mg. of penicillin amidase and 10 mg. of penicillin G (Na salt) were admixed to form a solution. During admixing the viscosity of the solution increased until after about 10 minutes following contacting of the reagents, the solution could no longer be stirred by hand. After one hour the solution was a hard solid material which was ground and screened to yield particles less than 840 micrometers in size. On a dry weight basis the activity of the particles was 1,020 units/g. Activity was defined as the micromoles of penicillin G split per minute at 30° C. at pH 8.

It is believed that other proteins will react with the prepolymer to form biologically active solid polymers, assuming the proteins are present in the prepolymer solution in large enough amounts. Presently, there is no way to determine in advance which protein will react with the prepolymer to form solids or at what levels the proteins must be employed in the solution. However, given our basic discovery, i.e., that protein/prepolymer solutions can be formed without destroying the biological activity of the protein, for any protein, solid formation can be determined simply by dissolving the protein at successively larger levels in different batches of prepolymer. Given the teaching of the present invention the above test can easily be performed by one of ordinary skill in enzyme chemistry. Once it is decided to immobilize a particular protein in active form by binding it to a polyurethane matrix, it is a simple matter to form solutions using increasingly large levels of protein as solute and determine if solid formation occurs. Conversely, if solid formation is to be avoided the above test can also be performed to determine the maximum binding level of proteins.

The above-mentioned U.S. Pat. No. 3,672,955 teaches that proteins (enzymes) can be bound to isocyanate-capped polyurethanes. In the process of said patent the isocyanate-capped polyurethane is dissolved in a water-immiscible solvent. This solution is emulsified, using an emulsifying agent, in the presence of an active enzyme which is dispersed in water.

Our process is similar in some respects to that of Stanley's said U.S. Pat. No. 3,672,955. We can use the same isocyanate-capped polyurethane prepolymer (which that patent refers to as polyisocyanates); we can use the same polyols (to prepare our prepolymer); and we can use the same enzymes. As in that patent (although we do not wish to be bound to any particular theory) the mechanism is apparently the reaction of one or more amine and/or hydroxyl groups on the protein with one or more isocyanate groups on the polyurethane prepolymer molecule.

As in the Stanley patent, our isocyanate-capped liquid polyurethane prepolymers can be prepared by reacting a polyol with a polyisocyanate using an excess of the isocyanate to ensure the presence of free (unreacted) isocyanate groups on the polyurethane prepolymer molecules.

Our process is also similar in some respects to that of the above-mentioned U.S. Pat. No. 3,929,574 (Wood et al). We can use the same isocyanate-capped polyurethane prepolymer (which that application refers to as an isocyanate-capped polyurethane), and we can use the same proteins (enzymes).

However, unlike the process of said U.S. Pat. No. 3,929,574, we admix our prepolymer and our enzyme under substantially water-free conditions. Said application admixes its prepolymer with an aqueous dispersion of an enzyme.

Any liquid polyurethane prepolymer, including those taught by said U.S. Pat. No. 3,929,574, which contains at least one free isocyanate group per prepolymer molecule is suitable for binding proteins in accordance with this invention. We prefer that the prepolymer contain an average of one to two isocyanate groups per molecule. An even higher ratio can be used, for example, 2–8 isocyanate groups per polyurethane molecule. Ratios higher than this are operable, but offer no advantage. Any excess isocyanate groups left in the protein/prepolymer solution (after binding of the protein) will be destroyed by hydrolysis upon dispersion of the solution into water.

The isocyanate-capped (isocyanate-terminated) liquid polyurethane prepolymers used in this invention contain at least two isocyanate groups (reactive isocyanate groups) per molecule of prepolymer. An isocyanate-capped polyurethane prepolymer is a "liquid polyurethane prepolymer" if: (a) it is a free flowing liquid at 40°–70° C.; or if it will dissolve in an inert solvent (e.g. an inert solvent such as those listed supra including those taught by Stanley) to form a solution containing about 1–50% (or 10–25%) by weight of isocyanate-capped polyurethane prepolymer.

As used herein, the term "liquid isocyanate-capped polyurethane prepolymer" means a liquid polyurethane or polyurea molecule containing at least about two free isocyanate groups per molecule.

Representative examples of polyisocyanates which can be reacted with an active hydrogen-containing compound (e.g. a glycol, polyol, polyglycol, polyester polyol, polyether polyol, and the like) to make an isocyanate-capped polyurethane in accordance with the invention include those listed in Table 1.

TABLE 1 toluene-2,4-diisocyanate
toluene-2,6-diisocyanate
commercial mixtures of toluene-2,4- and 2,6-diisocyanates
ethylene diisocyanate
ethylidene diisocyanate
propylene-1,2-diisocyanate
cyclohexylene-1,2-diisocyanate
cyclohexylene-1,4-diisocyanate
m-phenylene diisocyanate
3,3'-diphenyl-4,4'-biphenylene diisocyanate
4,4'-biphenylene diisocyanate
3,3'-dichloro-4,4'-biphenylene diisocyanate
1,6-hexamethylenediisocyanate
1,4-tetramethylene-diisocyanate
1,10-decamethylenediisocyanate
1,5-naphthalenediisocyanate
cumene-2,4-diisocyanate
4-methoxy-1,3-phenylenediisocyanate
4-chloro-1,3-phenylenediisocyanate
4-bromo-1,3-phenylenediisocyanate
4-ethoxy-1,3-phenylenediisocyanate
2,4'-diisocyanatodiphenylether
5,6-dimethyl-1,3-phenylenediisocyanate
2,4-dimethyl-1,3-phenylenediisocyanate
4,4'-diisocyanatodiphenylether
benzidinediisocyanate
4,6-dimethyl-1,3-phenylenediisocyanate
9,10-anthracenediisocyanate
4,4'-diisocyanatodibenzyl
3,3'-dimethyl-4,4'-diisocyanatodiphenylmethane
2,6-dimethyl-4,4'-diisocyanatodiphenyl
2,4-diisocyanatostilbene
3,3'-dimethyl-4,4'-diisocyanatodiphenyl
3,3'-dimethoxy-4,4'-diisocyanatodiphenyl
1,4-anthracenediisocyanate
2,5-fluorenediisocyanate
1,8-naphthalenediisocyanate
2,6-diisocyanatobenzfuran
2,4,6-toluenetriisocyanate
p,p',p''-triphenylmethane triisocyanate A useful class of liquid isocyanate-capped polyurethane prepolymers are those derived from polyether polyols and polyester polyols. These compounds may be prepared, as is well known in the art, by reacting a polyether (or polyester) polyol with a polyisocyanate, using an excess of the latter to ensure provision of free isocyanate groups in the product. A typical, but by no means limiting, example is illustrated in idealized equation form below:

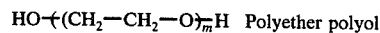  Polyether polyol

-continued

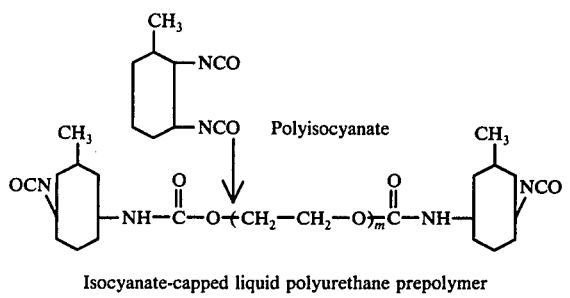

Isocyanate-capped liquid polyurethane prepolymer (In the above formulas, m represents the number of oxyethylene repeating units. This may range, for example, about from 5 to 50).

The compounds useful for the purposes of the invention may be prepared by reacting any of the above-exemplified polyisocyanates with any of a wide variety of polyols including: (a) simple polyols such as those listed in Table 2, infra; and (b) polyether polyols and polyester polyols. Representative examples of these polyols are described below.

Among the polyether polyols which may be so used are those prepared by reaction of an alkylene oxide with an initiator containing active hydrogen groups, a typical example of the initiator being a polyhydric alcohol such as ethylene glycol; a polyamine such as ethylene diamine; phosphoric acid, etc. The reaction is usually carried out in the presence of either an acidic or basic catalyst. Examples of alkylene oxides which may be employed in the synthesis include ethylene oxide, propylene oxide, any of the isomeric butylene oxides, and mixtures of two or more different alkylene oxides such as mixtures of ethylene and propylene oxides. The resulting polyether polyols contain a polyether backbone and are terminated by hydroxyl groups. The number of hydroxyl groups per polymer molecule is determined by the functionality of the active hydrogen initiator. For example, a difunctional alcohol such as ethylene glycol (as the active hydrogen initiator) leads to polyether chains in which there are two hydroxyl groups per polymer molecule. When polymerization of the oxide is carried out in the presence of glycerol, a trifunctional alcohol, the resulting polyether molecules contain an average of three hydroxyl groups per molecule. Even higher functionality—more hydroxyl groups—is obtained when the oxide is polymerized in the presence of such polyols as pentaerythritol, sorbitol, sucrose, dipentaerythritol, and the like. In addition to those listed above, other examples of polyhydric alcohols which may be reacted with alkylene oxides to produce useful polyether polyols include those listed in Table 2.

TABLE 2 propylene glycol
trimethylene glycol
1,2-butylene glycol
1,3-butanediol
1,4-butanediol
1,5-pentanediol
1,2-hexylene glycol
1,10-decanediol
1,2-cyclohexanediol
2-butene-1,4-diol
3-cyclohexene-1,1-dimethanol
4-methyl-3-cyclohexene-1,1-dimethanol
3-methylene-1,5-pentanediol
diethylene glycol
(2-hydroxyethoxy)-1-propanol
4-(2-hydroxyethoxy)-1-butanol
5-(2-hydroxypropoxy)-1-pentanol
1-(2-hydroxymethoxy)-2-hexanol
1-(2-hydroxypropoxy)-2-octanol
3-allyloxy-1,5-pentanediol
2-allyloxymethyl-2-methyl-1,3-propanediol
[(4-pentyloxy)methyl]-1,3-propanediol
3-(o-propenylphenoxy)-1,2-propanediol
thiodiglycol
2,2'-[thiobis(ethyleneoxy)]diethanol
polyethyleneether glycol (molecular weight about 200)
2,2'-isopropylidenebis(p-phenyleneoxy)diethanol
1,2,6-hexanetriol
1,1,1-trimethylolpropane
3-(2-hydroxyethoxy)-1,2-propanediol
ethylene glycol
3-(2-hydroxypropoxy)-1,2-propanediol
2,4-dimethyl-2-(2-hydroxyethoxy)methylpentanediol-1,5
1,1,1-tris[(2-hydroxyethoxy)methyl]ethane
1,1,1-tris[(2-hydroxypropoxy)methyl]propane
triethanolamine
triisopropanolamine
resorcinol
pyrogallol
phloroglucinol
hydroquinone
4,6-di-tertiarybutyl catechol
catechol
orcinol
methylphloroglucinol
hexylresorcinol
3-hydroxy-2-naphthol
2-hydroxy-1-naphthol
2,5-dihydroxy-1-naphthol
bis-phenols such as 2,2-bis(p-hydroxyphenyl)propane and bis-(p-hydroxyphenyl)methane
1,1,2-tris-(hydroxyphenyl)ethane
1,1,3-tris-(hydroxyphenyl)propane An especially useful category of polyether polyols are the polyoxyethylene polyols HO−(−CH$_2$CH$_2$−O−)$_x$H in which x is an average number such that the polyol has an average molecular weight of up to about 1,000 (or about 2,000 or somewhat higher).

The polyester polyols which may be employed as precursors are most readily prepared by condensation polymerization of a polyol with a polybasic acid. The polyol and acid reactants are used in such proportions that essentially all the acid groups are esterified and the resulting chain of ester units is terminated by hydroxyl groups. Representative examples of polybasic acids for producing these polymers are oxalic acid, malonic acid, succinic acid, glutaric acid, adipic acid, pimelic acid, suberic acid, azelaic acid, sebacic acid, brassylic acid, thapsic acid, maleic acid, fumaric acid, glutaconic acid, α-hydromuconic acid, β-hydromuconic acid, α-butyl-α-ethylglutaric acid, α,β-diethylsuccinic acid, o-phthalic acid, isophthalic acid, terephthalic acid, hemimellitic acid, trimellitic acid, trimesic acid, mellophanic acid, prehnitic acid, pyromellitic acid, citric acid, benzenepentacarboxylic acid, 1,4-cyclohexane dicarboxylic acid, diglycollic acid, thiodiglycollic acid, dimerized oleic acid, dimerized linoleic acid, and the like. Representative examples of polyols for forming these polymers include ethylene glycol, 1,3-propylene glycol, 1,2-propylene glycol, 1,4-butylene glycol, 1,3-butylene glycol, 1,2-butylene glycol, butene-1,4 diol, 1,6-hexane diol, hexene-1,6-diol, 1,7-heptane diol, diethylene glycol, glycerine, trimethylol propane, 1,3,6-hexanetriol, trimethanolamine, pentaerythritol, sorbitol, and any of the other polyols listed herein above in connection with the preparation of polyether polyols.

On being intimately contacted with a protein such as an enzyme, antibody, antigen, or the like, an isocyanate-capped polyurethane prepolymer becomes chemically very active. Some of the free isocyanate groups of the prepolymer are believed to react with the amine groups of the protein, and subsequently when dispersed in water, any residual isocyanate groups react with water to give carbon dioxide and form amine groups on the polyurethane molecule. These latter amine groups may react with free isocyanate groups on neighboring polyurethane molecules, and this reaction (forming a urea linkage) will cause formation and growth (including cross-linking) of a poly(urea-urethane) polymer and may result in nondispersible molecules if the reactions proceed far enough.

The ratio of water to protein plus isocyanate-capped liquid polyurethane prepolymer is not critical.

Numerous uses for aqueous dispersions of proteins prepared by the method of our invention will be readily apparent to those skilled in the art in view of the increased stability and reduced antigenicity of said materials. The aqueous dispersions may also be employed as standards or controls in test procedures, e.g. stabilized glucose oxidase for use in an assay of serum glucose, or stabilized creatine phosphokinase (CPK) for use as a standard in assaying for serum CPK.

Enzymes of all types can be bound by the process of this invention. Such enzymes include:

| oxido reductases | lyases |
| transferases | isomerases |
| hydrolases | ligases |

Typical of the specific enzymes which can be immobilized (i.e., bound) according to the process of this invention are listed in Table 3.

| urease | cellulase |
| trypsin | ficin |
| lactase | bromelain |
| glucose oxidase | pancreatin |
| chymotrypsin | isoamylase |
| ribonuclease | lipase |
| peroxidase | malic dehydrogenase |
| pepsin | hexokinase |
| rennin | lactate dehydrogenase |
| invertase | adenosine deaminase |
| papain | uricase |
| asparaginase | galactose oxidase |
| pectinase | diaphorase |
| pectin esterase | cholinesterase |
| penicillin amidase | aldolase |
| glucose isomerase | pyruvate carboxylase |
| lysozyme | phospharylase |
| amine acid acylase | cephalosporin amidase |
| pronase | isocitric dehydrogenase |
| alcohol dehydrogenase | α-glycerolphosphate dehydrogenase |
| α-amylase | |
| β-amylase | glyceraldehyde-3-phosphate dehydrogenase |
| subtilisin | |
| amino acid oxidase | malic enzyme |
| catalase | glucose-6-phosphate dehydrogenase |

-continued

| tannase | |
| phenol oxidase | 5-dehydroshikimic reductase |
| glucoamylase | glutathione reductase |
| pullulanase | glycolic acid oxidase |
| yeast cytochrome c reductase | nitrate reductase |
| luciferase | xanthine oxidase |
| nitrite reductase | lipoyl dehydrogenase |
| glutamyl transferase | flavin peroxidase |
| glutathione synthetase | glycine oxidase |
| glycocyamine phosphokinase | carboxylase |
| hippuric acid synthetase | α-keto acid dehydrogenase |
| aldehyde oxidase | transketolase |
| succinic dehydrogenase | |

The instant invention will be better understood by referring to the following specific but nonlimiting examples and procedures. It is understood that said invention is not limited by these examples and procedures which are offered merely as illustrations; it is also understood that modifications can be made without departing from the spirit and scope of the invention.

The examples were actually run. The procedures, while not actually run, illustrate certain embodiments of our invention.

In the following examples the urethane prepolymer (Prepolymer) was prepared by admixing polyethylene glycol (PEG - M.W. about 1,000) with trimethylol propane (TMOP) and capping the admixture with toluene diisocyanate (TDI). The molar ratio of PEG/TMOP/TDI was about 2/0.66/6.3.

EXAMPLE 1

Lysozyme Bound to Polyurethane

A water-dispersible lysozyme/polyurethane reaction product was prepared by mixing together 0.1 g. of lysozyme and 1.0 g. of the Prepolymer. These materials were allowed to react for 1 hour in a desiccator at ambient temperature (approximately 70° F.)

The enzyme/polyurethane composition was slowly added to 500 ml. deionized water containing 3 drops of a poly(oxyethylene/oxypropylene) surfactant (Pluronic L-61). During addition the water was agitated rapidly. After all the composition had been added, it was stirred for an additional 35 minutes. The stirred material separated into two phases.

The soluble phase was separated by filtration through a Whatman #40 filter, then through a Millipore 0.22μ filter. From activity against *Micrococcus lysodeikticus*, it was determined that 50% of the enzyme activity was present in the soluble phase.

A control sample was prepared by curing and filtering 1.0 g. of prepolymer (without enzyme) as above.

Sephadex G-50 (fine) was swollen in 0.05 M. ammonium acetate buffer (pH 7.0), and used to fill a 2.5 × 45 cm. glass chromatography column for a finished column of 2.5 × 41 cm. Samples were eluted with 0.05 M. ammonium acetate buffer (pH 7.0) at 1.35 ml. min.$^{-1}$ at ambient temperature and collected in 4.5 ml. fractions. Absorbance at λ=280 nm. was read on each fraction. For each sample the absorbance was measured serially for 60 fractions eluted from the column. The samples were applied to the column as follows.

A 2.0 ml. sample of soluble polymer-bound lysozyme was applied to the column and eluted (as described). The soluble polymer-bound lysozyme peaked at fraction 37 with an absorbance of 0.1. The free polyurethane used as a control peaked at 41 and an absorbance of 0.12.

The shape of the absorbance curves for the polymer-bound enzyme and free polymer were similar and did not give sharp peaks as did the dextran and free enzyme. The relatively broad distribution and lack of a sharp peak is believed to reflect the presence of a broad distribution of polymer chain lengths in the bound enzyme and free polymer samples.

2.0 ml. sample containing 1.5 mg. free dextran m.w. about 2000) and 4 mg. free lysozyme was applied to the column and eluted with buffer. The dextran peaked at fraction 13 (absorbance 0.71) and free lysozyme at fraction 30 (absorbance 0.32).

EXAMPLE 2

Trypsin Bound to Polyurethane

Trypsin was bound to polyurethane to yield a water-dispersible product by mixing together 0.1 g. of trypsin and 0.9 g. of the Prepolymer and slowly adding the admixture into 500 ml. of deionized water as in the preceding example using lysozyme.

After filtration, and drying the insoluble material in a 45° C. drying oven, 32% of the initial material was recovered as being insoluble.

A control preparation was made as in the preceding example, but without enzyme.

Sephadex G-50 (fine) was swollen in deionized water and used to fill two 0.9 × 60 cm. chromatography columns linked in series by a small length of fine tubing, for a finished column height of 0.9 × 120 cm. Samples were eluted with deionized water at 0.3 ml. min.$^{-1}$ at ambient temperature and collected in 2.7 ml. fractions. Absorbance at $\lambda=280$ nm. was read on each fraction.

A 1.0 ml. sample of soluble-bound trypsin was applied to the column and eluted with deionized water. It gave two peaks absorbing at 280 nm., the minor peak in fraction 20, and the major peak in fraction 23.

A 1.0 ml. sample of the control was applied to the column and eluted with deionized water, giving a minor peak in fraction 18, and a major peak in fraction 21.

A 1.0 ml. sample containing 2 mg. free trypsin was applied to the column, and gave a single peak at fraction 20.

For the soluble bound trypsin the absorbance was about 190 nm. (major peak) and 173 nm. (minor peak). For the free trypsin the absorbance was about 213 nm. The absorbance for the polyurethane control was about 90 nm. (minor peak) and about 205 nm. (major peak).

EXAMPLE 3

Bovine Serum Albumin/Polyurethane Soluble Reaction Product

Bovine serum albumin (BSA) bound to polyurethane was prepared by mixing together 0.1 g. BSA with 0.9 g. of the Prepolymer and allowing them to react together in a desiccator (to keep dry) for one hour.

The above material was added slowly to 200 ml. of deionized water. The water was stirred rapidly during addition. After addition was complete, the aqueous dispersion was stirred for an additional 35 minutes.

The soluble fraction was separated by passing the material through a Whatman #40 filter, and then through a Millipore 0.22$\mu$ filter. The amount of insolubles (40% — based on the combined weight of enzyme and prepolymer) was determined by drying the residue present after filtration.

Samples of the soluble material, and equivalent levels of free BSA in deionized water, were applied to an Ampholine PAG plate (pH range 3.5–9.5) on an LKB Multiphor isoelectric focusing unit.

Electrofocusing was run at 10° C. until the pH gradient was completed. The gel plate containing the samples was then stained to visualize proteins.

Free BSA (reported to have pI = 4.9 in the literature) gave four detectable protein bands in the pH range 4.8–5.3. The sample containing the BSA/prepolymer reaction product gave one homogenous band in the pH range 4.8–5.0.

EXAMPLE 4

Invertase Bound to Polyurethane

Invertase (250 mg.) was dissolved in 4 g. of Prepolymer. The solution was slowly added to 300 ml. of $H_2O$ stirred at 1,000 RPM. The resulting dispersion was filtered. Both the aqueous phase and the solid residual phase were found to possess enzymatic activity.

Free invertase was dispersed in water to provide the same level of enzyme activity as the aqueous dispersion. The two aqueous dispersions (free-enzyme and bound-enzyme) were stored at 10° C. for 14 days with the activity levels of both dispersions decreasing by about 10%. Simultaneously a similar comparison was conducted only the dispersions were stored at 40° C. After 14 days the polymer-bound enzyme retained about 45% of its original activity whereas the free enzyme exhibited only trace amounts of activity amounting to less than 5% of the initial activity.

The aqueous dispersion of polymer-bound enzyme was more thermally stable at 40° C. than the free enzyme.

EXAMPLE 5

Trypsin Bound to Polyurethane

Precipitation with Trichloroacetic Acid

Preparation of soluble bound protein

Trypsin (400 mg.) was dissolved in the Prepolymer (3600 mg.) and was allowed to react at room temperature in a desiccator (dry) for 1 hour.

The reaction product was dispersed in water by adding to 200 ml. water in small increments with rapid stirring for 30 minutes.

Insoluble product was removed by filtering through Whatman #40 filter paper, followed by Millipore filtration using a 0.22$\mu$ filter.

The combined precipitates from both filtrations were dried and weighed. The difference (reactant weights less precipitates) was the amount of soluble material in the resultant 200 ml. of clear solution.

The above was repeated except no enzyme was used (i.e., 3600 mg. Prepolymer reacted with 200 ml. water). The resultant polymer solution after filtration served as the blank, i.e., polymer control solution.

Two other controls were made as follows: Control-1 contained 6 mg. trypsin dissolved in 10 ml. water; Control-2 contained 6 mg. trypsin dissolved in 10 ml. of the blank solution.

To solution (10 m.) of each of the above, 30 ml. of a 5% trichloroacetic acid solution was added. After 30 minutes at room temperature, the resultant products were centrifuged (30 minutes; 17,000 rpm.). Supernates were decanted and the resultant precipitates were dried in a vacuum oven.

The weights of the precipitates obtained, as well as the amount of material in each 10 ml. solution prior to precipitation were:

| Sample | Amount of Material in Solution | Protein in Solution | Protein in Solution | Precipitate |
|---|---|---|---|---|
| Blank | 72 | 0 | 72 | 2 |
| Control-1 | 6 | 6 | 0 | 8 |
| Control-2 | 78 | 6 | 72 | 9 |
| Soluble Bound | 59 | (6)* | (53)* | 25 |

*Calculated from the known amount in solution (obtained as reactants less initial filration) using the ratio of prepolymer/enzyme in the reaction mixture.

TCA is a known reagent for precipitating proteins, whereas it is herein shown it does not precipitate soluble polyurethane. When TCA is added to soluble bound proteins, the protein precipitates out, bringing along with it that portion of the soluble polyurethane which was bound thereto.

Similar runs were carried out with BSA and penicillin amidase. The results are set forth below.

| BSA/Trichloroacetic Acid Precipitation | | | | |
|---|---|---|---|---|
| | Total | Protein | Polymer | Precipitate |
| Blank | 62 | 0 | 62 | 2 |
| Control-1 | 8 | 8 | 0 | 11 |
| Control-2 | 70 | 8 | 62 | 16 |
| Soluble Bound | 80 | (8)$^a$ | (72)$^a$ | 23 |
| Penicillin Amidase/Trichloracetic Acid Precipitation | | | | |
| | Total | Protein | Polymer | Precipitate |
| Blank | 62 | 0 | 62 | 0 |
| Control-1 | 8 | 8 | 0 | 8 |
| Control-2 | 70 | 8 | 62 | 12 |
| Soluble Bound | 77 | (7)$^a$ | (70)$^a$ | 20 |

$^a$ Calculated as described above for trypsin.

What is claimed is:

1. A method for preparing an aqueous solution of protein bound to a urethane polymer comprising:
   a. admixing a water-dispersible, biologically-active protein and an isocyanate-capped liquid polyurethane prepolymer having an oxyalkylene backbone containing at least 50 mole % of oxyethylene units under essentially anhydrous conditions to form a solution, said protein and prepolymer reacting to form a water-soluble reaction product wherein the protein and prepolymer are bound together; and
   b. dispersing the solution in water with agitation to form an aqueous solution of urethane-polymer bound protein.

2. A method as in claim 1 wherein the aqueous solution of protein bound to urethane polymer is filtered.

3. A method as in claim 1 wherein the protein is an enzyme.

4. An aqueous solution of a water-dispersible, biologically-active protein bound to a polyurethane characterized as having an essentially linear polyoxyalkylene backbone containing at least 50 mole % of oxyethylene units, said protein bound to said polyurethane through a ureido linkage, said polyurethane-bound protein being water-soluble.

5. An aqueous solution as in claim 4 wherein the protein is an enzyme.

6. An aqueous solution of a water-dispersible, biologically-active protein bound to a polyurethane, said bound protein formed by dissolving the protein in an isocyanate-capped liquid polyurethane prepolymer under essentially anhydrous conditions to form a solution, said protein and prepolymer reacting to form a water-soluble reaction product wherein the protein and prepolymer are bound together; said prepolymer having an essentially linear oxyalkylene backbone containing at least 50 mole % oxyethylene units;

and dispersing the solution in water with agitation to form a solution of polyurethane bound protein.

7. An aqueous solution as in claim 6 wherein the protein is an enzyme.

8. An aqueous solution of a water-dispersible, biologically-active protein bound to a polyurethane characterized as having an essentially linear polyester backbone, said protein bound to said polyurethane through a ureido linkage, said polyurethane-bound protein being water-soluble.

9. An aqueous solution as in claim 8 wherein the protein is an enzyme.

10. A method for preparing an aqueous solution of protein bound to a urethane polymer comprising:
    a. admixing a water-dispersible, biologically-active protein and an isocyanate-capped liquid polyurethane prepolymer having a linear polyester backbone under essentially anhydrous conditions to form a solution, said protein and prepolymer reacting to form a water-soluble reaction product wherein the protein and prepolymer are bound together; and
    b. dispersing the solution in water with agitation to form an aqueous solution of urethane-polymer bound protein.

11. A method as in claim 10 including a step of filtering the aqueous solution to remove nondispersible protein/polyurethane compounds.

12. A method as in claim 10 wherein the protein is an enzyme.

13. A method for preparing an aqueous dispersion of enzyme bound to a urethane polymer comprising:
    a. dispersing an enzyme in an isocyanate-capped liquid polyurethane prepolymer under essentially anhydrous conditions to form a solution;
    b. forming a dispersion by slowly adding said enzyme/polyurethane composition to water while agitating, and continuing agitation following addition of said composition; and
    c. separating insoluble bound enzymes from the aqueous dispersion.

14. A method for preparing an aqueous solution of protein bound to a urethane polymer comprising:
    a. dispersing of biologically-active protein in an isocyanate-capped liquid polyurethane prepolymer under essentially anhydrous conditions to form a solution; and
    b. dispersing the solution in water with agitation to form a solution of urethane polymer-bound protein.

15. A method as in claim 14 wherein the polyurethane has a polyoxyalkylene backbone.

16. A method as in claim 15 wherein the backbone contains at least 50 mole % of oxyethylene units.

17. A method as in claim 14 wherein the polyurethane has a polyester backbone.

18. A method as in claim 14 wherein the solution is dispersed with the aid of a surfactant.

19. A method as in claim 14 wherein the prepolymer is dissolved in a water-immiscible organic solvent and the protein is dissolved in said prepolymer/solvent solution to form the solution of part a of claim 14.

* * * * *